United States Patent
Andersson et al.

(10) Patent No.: US 7,189,368 B2
(45) Date of Patent: Mar. 13, 2007

(54) FUNCTIONAL UNIT ENABLING CONTROLLED FLOW IN A MICROFLUIDIC DEVICE

(75) Inventors: Per Andersson, Uppsala (SE); Gunnar Thorsen, Stockholm (SE); Gunnar Kylberg, Bromma (SE)

(73) Assignee: Gyros Patent AB, Uppsala (SE)

( * ) Notice: Subject to any disclaimer, the term of this patent is extended or adjusted under 35 U.S.C. 154(b) by 536 days.

(21) Appl. No.: 10/244,867

(22) Filed: Sep. 17, 2002

(65) Prior Publication Data

US 2003/0053934 A1    Mar. 20, 2003

Related U.S. Application Data

(63) Continuation-in-part of application No. PCT/SE02/00537, filed on Mar. 19, 2002.

(60) Provisional application No. 60/322,621, filed on Sep. 17, 2001.

(30) Foreign Application Priority Data

Sep. 17, 2001 (SE) ..................... 0103117

(51) Int. Cl.
*B01L 3/02* (2006.01)
*B01L 11/00* (2006.01)
*B32B 5/02* (2006.01)
*B32B 27/04* (2006.01)
*B32B 27/12* (2006.01)

(52) U.S. Cl. ............... 422/100; 422/101; 422/102; 422/103; 422/104; 436/43; 436/174; 436/177; 436/180

(58) Field of Classification Search ............... 422/100, 422/101, 102, 103, 104; 436/43, 174, 177, 436/180
See application file for complete search history.

(56) References Cited

U.S. PATENT DOCUMENTS 5,160,702 A    11/1992   Kopf-Sill et al.

(Continued)

FOREIGN PATENT DOCUMENTS

WO    IB-95/06870 A1    3/1995

(Continued)

OTHER PUBLICATIONS

WO 98/07019. Kellogg et al. Feb. 19, 1998.*

(Continued)

*Primary Examiner*—Brian Sines
(74) *Attorney, Agent, or Firm*—Fulbright & Jaworski L.L.P.

(57) ABSTRACT

A microfluidic device which comprises two or more microchannel structures (set 1), each of which comprises a structural unit which comprises (i) one or more inlet microconduits, and (ii) an outlet microconduit downstream said one or more inlet microconduits, and (iii) a flow path for a liquid passing through either of said inlet microconduits and said outlet microconduit. The device is characterized in that each outlet microconduit in said two or more microchannel structures is a restriction microconduit. There may also be a microcavity between the inlet microconduit(s) and the restriction microconduit in each microchannel structure. Typically common flow control is used for driving a liquid flow within the device. The innovative design is useful for creating flow with low inter-channel variation with respect to the microchannel structures of the device.

31 Claims, 4 Drawing Sheets

U.S. PATENT DOCUMENTS

| | | | |
|---|---|---|---|
| 5,472,603 | A | 12/1995 | Schembri |
| 6,418,968 | B1 | 7/2002 | Pezzuto et al. |
| 6,481,453 | B1 * | 11/2002 | O'Connor et al. ........ 137/15.04 |
| 6,561,208 | B1 * | 5/2003 | O'Connor et al. ........ 137/15.18 |
| 6,637,463 | B1 * | 10/2003 | Lei et al. .................... 137/803 |
| 6,709,869 | B2 * | 3/2004 | Mian et al. .................... 436/45 |
| 2002/0153046 | A1 | 10/2002 | Dantsker et al. |

FOREIGN PATENT DOCUMENTS

| | | |
|---|---|---|
| WO | IB-95/33986 A1 | 12/1995 |
| WO | IB-97/21090 A1 | 6/1997 |
| WO | IB-98/07019 A1 | 2/1998 |
| WO | IB-98/53311 A2 | 11/1998 |
| WO | IB-99/55827 A1 | 11/1999 |
| WO | IB-99/58245 A1 | 11/1999 |
| WO | IB-00/25921 A1 | 5/2000 |
| WO | IB-00/40750 A1 | 7/2000 |
| WO | WO 00/40750 | 7/2000 |
| WO | IB-00/50172 A1 | 8/2000 |
| WO | IB-00/56808 A2 | 9/2000 |
| WO | IB-00/62042 A1 | 10/2000 |
| WO | IB-01/46465 A2 | 6/2001 |
| WO | IB-01/46465 A3 | 6/2001 |
| WO | WO 01/46465 A2 | 6/2001 |
| WO | WO 01/46465 A3 | 6/2001 |
| WO | IB-01/47637 A1 | 7/2001 |
| WO | IB-01/47638 A2 | 7/2001 |
| WO | WO 01/47638 A2 | 7/2001 |
| WO | WO 01/47638 A3 | 7/2001 |
| WO | IB-01/54810 A1 | 8/2001 |
| WO | IB-01/87486 A2 | 11/2001 |
| WO | IB-01/87487 A2 | 11/2001 |
| WO | IB-02/41997 A1 | 5/2002 |
| WO | IB-02/41998 A1 | 5/2002 |
| WO | WO 02/41997 A1 | 5/2002 |
| WO | WO 02/41998 A1 | 5/2002 |
| WO | IB-02/074438 A2 | 9/2002 |
| WO | IB-02/075312 A1 | 9/2002 |
| WO | IB-02/075775 A1 | 9/2002 |
| WO | IB-02/075776 A1 | 9/2002 |
| WO | WO 02/075775 A1 | 9/2002 |
| WO | WO 02/075776 A1 | 9/2002 |

OTHER PUBLICATIONS

Tooke, Nigel, et al.; High-throughput SNP scoring in a microfabricated CD device; Amersham Pharmacia Biotech, Uppsala, Sweden.

Sato, Kiichi, et al.; Integration of an Immunosorbent Assay System: Analysis of Secretory Human Immunoglobulin A on Polystyrene Beads in a Microchip; Anal. Chem. 72:1144-1147, 2000.

Eteshola, E., et al.; Development and characterization of an ELISA assay in PDMS microfluidic channels; Sensors and Actuators B 72:129-133, 2001.

Microfluidics in a Rotating CD; presented at MICROTAS 2000, Enschede, The Netherlands, May 14-18, 2000.

High-Throughput SNP Scoring in a Disposable Microfabricated CD Device; presented at HGM 2000, Vancouver, Canada, Apr. 9-12, 2000.

PCT International Preliminary Examination Report—International Application No. PCT/SE02/01701.

Tooke et al, "High-Throughput SNP Scoring in a disposable Micro-Fabricated CD Device Combined with Solid-Phase Pyrosequencing," Human Genome Meeting, HGM 2000, Vancouver, Canada, Apr. 9-12.

Ekstrand, et al., Microfluidics in a Rotating CD; Gyros Technology, Presentations for Download.

Eckersten et al., High-Throughput SNP Scoring in a Disposable Microfabricated CD Device; Gyros Technology, Presentations for Download.

Tooke et al., High-Throughput SNP Scoring in a Disposable Microfabricated CD Device Combined with Solid Phase Pyrosequencing; Gyros Technology, Presentations for Download.

Tooke et al., High-Throughput SNP Scoring in a Disposable Microfabricated CD Device; Gyros Technology, Presentations for Download.

* cited by examiner

FUNCTIONAL UNIT ENABLING CONTROLLED FLOW IN A MICROFLUIDIC DEVICE

This application is a continuation in part of International Application No. PCT/SE02/00537, which was filed on Mar. 19, 2002; and claims priority to Swedish Application No. 0103117-8, which was filed on Sep. 17, 2001 and U.S. Provisional Application No. 60/322,621, which was filed on Sep. 17, 2001.

BACKGROUND OF THE INVENTION

A. Field of Invention

The present invention relates to a microfluidic device which comprises two or more microchannel structures (e.g., set 1, set 2, set 3), each of which comprises one or more inlet ports, one or more outlet ports, and a structural unit which is located between an inlet port and an outlet port. The structural unit comprises one or more inlet microconduits, each of which communicates with an inlet port, and an outlet microconduit, which communicates with an outlet port, and an microcavity, which is located between said inlet port and said outlet port. More particularly, the structural unit starts at the inlet ends of the inlet microconduits and ends at the outlet end of the outlet microconduit and includes valves and anti-wicking means that may be present at the end parts.

B. Related Art

Typically, microfluidic devices that comprise the above-mentioned structural unit have not comprised any means that will secure parallelity with a low inter-channel variation in flow rate between individual microchannel structures. The residence time for reactants within the individual microcavities and elsewhere in the microchannel structures has typically varied in an unintended manner within wide limits. Depending on kind of reactants, for instance, this may heavily influence the results obtained.

Magnus Gustavsson et al., (Gyros AB) have presented experiments comprising parallel reaction (adsorption) in a microfluidic device ("Integrated sample preparation and MALDI MS on a microfluidic compact disc (CD with improved sensitivity", ASMS 2001). This presentation described a MALDI MS integrated microfluidic affinity system based on adsorbing a protein digest to a reverse phase matrix and subsequent desorption and transport of peptides to a combined outlet port/MALDI MS target. The demands on reproducibility in binding, the control of liquid flow rate, and the residence time were low. Harrison et al., (WO 0138865, University of Alberta) have described a solid phase extraction method in a singular microchannel structure by affinity binding under flow conditions. Eteshola et al., (Sensors and Actuators B 72 (2001) 129–133), Sato et al., (Anal. Chem. 72 (2000) 1144–1147); and Mian et al., (WO 9721090, Gamera Biosciences), for instance, have described performing affinity reactions under non-flow conditions in microcavities.

The use of centrifugal force for moving liquids within microfluidic systems has also been described for instance by Abaxis Inc (WO 9533986, WO 9506870, U.S. Pat. No. 5,472,603); Molecular devices (U.S. Pat. No. 5,160,702); Gamera Biosciences/Tecan (WO 9721090, WO 9807019, WO 9853311), WO 01877486, WO 0187487; Gyros AB/Amersham Pharmacia Biotech (WO 9955827, WO 9958245, WO 0025921, WO 0040750, WO 0056808, WO 0062042, WO 0102737, WO 0146465, WO 0147637, WO 0147638, WO 0154810, WO 0241997, WO 0241998, PCT/SE02/00531, PCT/SE02/00537, PCT/SE02/00538, PCT/SE02/00539 and PCT/SE02/01539. See also presentations made by Gyros AB at various scientific meetings: High-through put screening SNP scoring in microfabricated device, Nigel Tooke (September 99); Microfluidics in a rotating CD (Ekstrand et al.) MicroTAS 2000, Enschede, The Netherlands, May 14–18, 2000; SNP scoring in a disposable microfabricated CD device (Eckersten et al.) and SNP scoring in a disposable microfabricated CD device combined with solid phase Pyrosequencing™ (Tooke et al.) Human Genome Meeting, HGM 2000, Vancouver, Canada, Apr. 9–12, 2000; and Integrated sample preparation and MALDI MS on a microfluidic compact disc (CD with improved sensitivity (Magnus Gustavsson et al.) ASMS 2001 (spring 2001).

The publications above in the name Gyros AB or Amesham Pharmacia Biotech primarily concerns nl-volumes and problems associated therewith while the other publications primarily aims at µl-volumes or larger.

BRIEF SUMMARY OF THE INVENTION

The present invention is drawn to a microfluidic device which comprises two or more microchannel structures (e.g., set 1, set 2, set 3), each of which comprises one or more inlet ports, one or more outlet ports, and a structural unit which is located between an inlet port and an outlet port. The structural unit comprises one or more inlet microconduits, each of which communicates with an inlet port, and an outlet microconduit, which communicates with an outlet port, and an microcavity, which is located between said inlet port and said outlet port. More particularly, the structural unit starts at the inlet ends of the inlet microconduits and ends at the outlet end of the outlet microconduit and includes valves and anti-wicking means that may be present at the end parts.

A further embodiments is that a liquid aliquot passes through the structural unit of the present invention via at least one of the inlet microconduits, the microcavity and the outlet microconduit of the structural unit.

Yet further, the microchannel structures of at least one set of microchannel structures are identical in the sense that corresponding parts in the individual microchannel structures are essentially identical. More particularly, the microfluidic device may also comprise one or more additional sets of identical microchannel structures that are not identical to first set of microchannel structures.

In further embodiments of the present invention, reactions may be performed in the microcavities or downstream, for instance in and/or downstream the outlet microconduit.

Another embodiment of the present invention is a method for creating a controlled liquid flow in parallel through a plurality of microchannel structures of a microfluidic device, said method comprises the steps of: (a) providing a microfluidic device which comprises said plurality of microchannel structures, each of which comprises a structural unit which comprises one or more inlet microconduits, an outlet microconduit downstream said one or more inlet microconduits, and a flow path for a liquid passing through either of said inlet microconduits and said outlet microconduit; (b) providing a liquid aliquot in at least one of said one or more inlet microconduits in each of the microchannel structures; and (c) applying a driving force that creates a liquid flow that transport each of said aliquot through the outlet microconduit in each of the microchannel structures; wherein the outlet microconduits are restriction microconduits, the liquid flow created in step (c) is under common flow control, and the flow rate created in step (c) for each of the structural units is adjusted to give the pressure drop in the restriction microconduits.

The present invention recognizes that the presence of means for creating a significant pressure drop (pressure drop means, flow restriction means) in the outlet microconduit, possibly combined with pressure drop means in the microcavity, if present and common flow control for the liquid flow in the different microchannel structures/structural units are of benefit for controlling the liquid flow in the microchannel structures/structural units of the microfluidic device.

Significant pressure drop contemplates that the pressure drop at these locations is larger than the total inter-channel variation in flow resistance emanating from positions upstream and downstream the locations concerned in the structural units (primarily upstream the outlet microconduit). The term "restriction microconduit" designates outlet microconduits that comply with this criterion.

Yet further, the present invention has also recognized that further benefits may be accomplished if one or more of the following features are also complied with the inventive microfluidic device: (a) porous matrix is placed in the microcavity or immediately downstream this microcavity for creating a significant pressure drop along the matrix; (b) packed bed of monosized particles instead of polysized particles in the microcavity will lower the inter-channel variation in pressure drop along the microcavity; (c) pulse giving increased flow will assist in overcoming inter-channel variations in flow resistance of the individual microchannel structures (this in particular applies when initiating flow and/or when the liquid is to pass through branchings and curvatures); and (d) an anti-wicking means in inner edges downstream and in close proximity to the outlet end of the outlet microconduit, which leads waste liquids from the microcavity.

The microcavity (105,205) may also contain a solid phase with an immobilized affinity reactant, which is to react with an affinity counterpart that is present as a solute in the liquid flow. The product obtained is an immobilized affinity complex. For these variants the inventors have recognized benefits for: (e) excess of solid phase affinity reactant (immobilized reactant) in the reaction microcavity; and (f) selecting flow rates that accomplish residence times $\geq 0.010$ seconds for the formation of complex in the reaction microcavity. It is also envisioned that similar effects will also be accomplished for other immobilized reactants and heterogeneous reactions. Residence time refers to the time it takes for a liquid aliquot to pass through the microcavity (e.g., comprising a solid phase).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIGS. 2A and 2B are identical except that FIG. 2A gives the dimensions and FIG. 2B hydrophobic surface breaks and their dimensions.

The structures shown in FIGS. 2–3 are intended for a circular disc in which the microchannel structures are placed around its axis of symmetry that also can be used as a spin axis. The arrow shows the direction towards the center of the disc. Note the arc-like configuration. FIGS. 2–3 also show the dimensions in micro-meter of various parts of the structures.

DETAILED DESCRIPTION OF THE INVENTION

A first object of the present invention is to provide a fluidic function that when incorporated into a set of microchannel structures of a microfluidic device will standardize the flow rate through the microcavity, if present, and the outlet microconduit of the microchannel structures of the set, i.e., to control the flow rate such that the inter-channel variation in flow rate is reduced to an acceptable level.

A second object of the present invention is to provide a robust microfluidic system that can be used for performing a plurality of experiments in parallel for determining reaction variables, e.g., as described in PCT/SE02/00537. Typically the determination concerns finding the content of analytes in samples and new and/or optimal binder-ligand combinations, and/or to grade affinity for a range of affinity complexes, ligands and binders, and/or to optimize processes involving formation or dissociation of immobilized affinity complexes under flow conditions.

A third object of the present invention is to provide a device and a method for creating a parallel liquid flow with a low inter-channel variation in flow rate through a set of microchannel structures of a microfluidic device.

A fourth object of the present invention is to provide a structural unit that enables a microfluidic device which comprises two or more sets of microchannel structures which permits parallel liquid flow with a low inter-channel variation within the individual sets and well defined differences in flow rates between the sets. One set, for instance, may represent a particular liquid flow rate in a particular step of an application carried out within the structures, while another set represent another different flow rate for the corresponding step. This object also includes a microfluidic device comprising this kind of structural units.

A. Structural Unit

The first aspect of the invention thus relates to a structural unit and a microfluidic device. The structural unit comprises one or more inlet microconduits, each of which communicates with an inlet port, and an outlet microconduit, which communicates with an outlet port, and an microcavity, which is located between said inlet port and said outlet port. More particularly, the structural unit starts at the inlet ends of the inlet microconduits and ends at the outlet end of the outlet microconduit and includes valves and anti-wicking means that may be present at the end parts.

Figure 1:
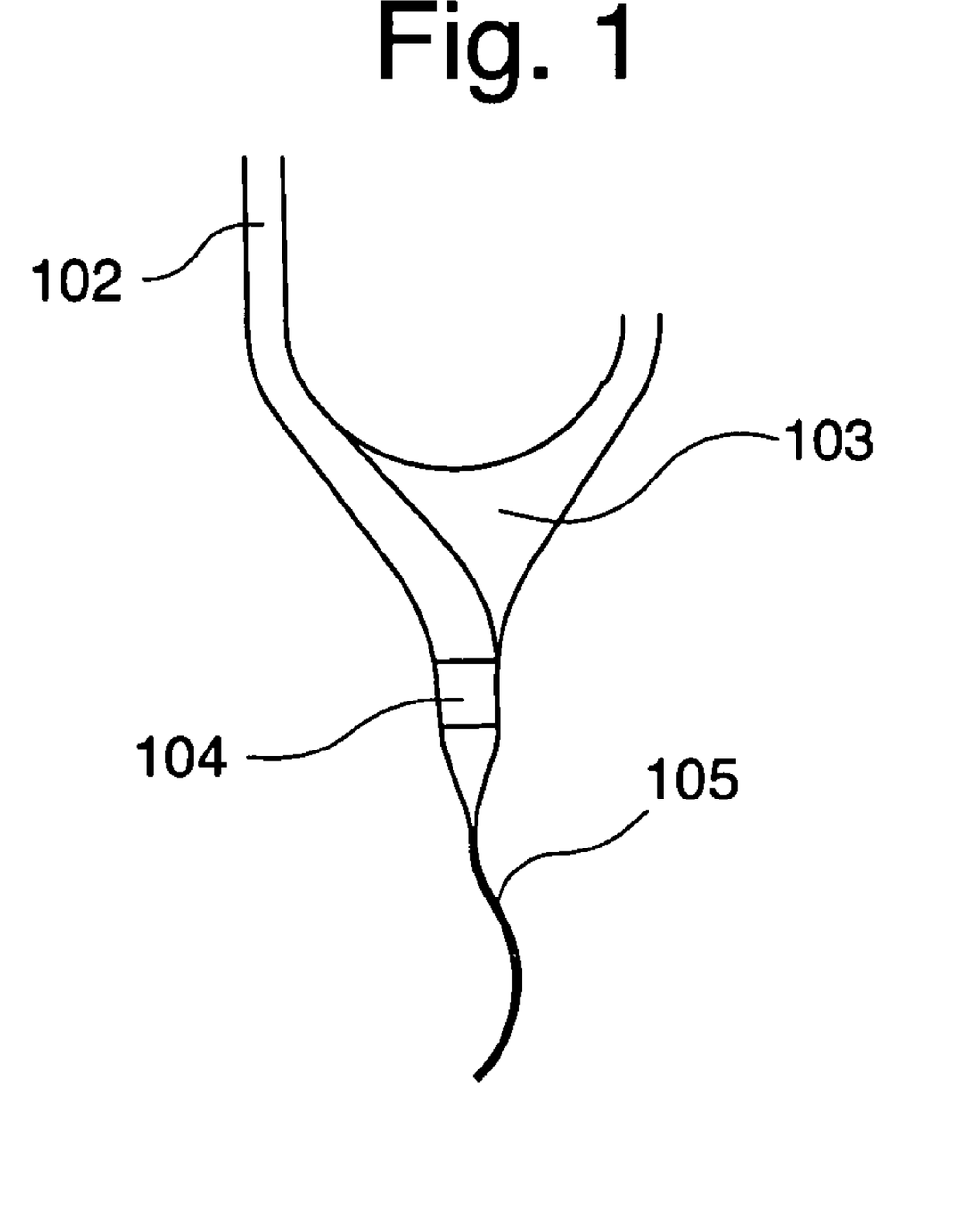
FIG. 1 illustrates the key part of a structural unit that comprises a microcavity and means for creating a pressure drop.

Yet further, the structural unit and also the microfluidic device are characterized in that there are means for creating a significant pressure drop in the outlet microconduits (105, 205,305) (restriction microconduit) and possibly also in the microcavities (104,204,304), if present. The flow through the individual microchannel structures, in particular the inventive structural units (as shown in FIG. 1), on a microfluidic device is preferably under common flow control.

1. Means for Creating Pressure Drop

In addition to leveling out the above-mentioned inter-channel variation in flow resistance, these means may also create a pressure drop that is larger than the total resistance to flow upstream the location comprising the pressure drop means, for instance upstream the microcavity (104,204,304) or restriction microconduit (but within the structural unit). Typically, the microchannel structures are designed such that the flow resistance and inter-channel variations in flow resistance at the end of the restriction microconduits (206, 306) and/or in other downstream positions are insignificant compared to the upstream part of a structural unit.

The inter-channel variations in flow resistance and pressure drop for the structural unit of different microchannel structures primarily depend on (a) variations in inner surface characteristics upstream the microcavity (104,204,304), (b) variations in the solid phase used (for instance the packing geometry may differ), and (c) design around the outlet end (206) and surface variations in other positions downstream the restriction microconduit (205).

Significant pressure drop and/or significant flow resistance in positions upstream and downstream the restriction microconduit are only at hand in parts that contain liquid. This means that the pressure drop upstream the inlet microconduit(s) is negligible, for instance.

The pressure drop means in the outlet microconduit (restriction microconduit) and/or in the microcavity should give an inter-channel variation in residence time for a liquid aliquot within the intervals of mean residence time ±90%, such as ±75% or ±50% or ±25% for essentially identical microchannel structures for which the driving force for the liquid flow is essentially the same.

The appropriate flow rate through and residence time in the reaction microcavity depends on a number of factors which among others are determined by the purpose of the passage through the microcavity, for instance kind of reaction to take place, the volume of the microcavity, possible presence and form of a the solid phase, etc. The flow rate applied should in most cases give a residence time of $\geq 0.010$ seconds such as $\geq 0.050$ sec or $\geq 0.1$ sec with an upper limit that typically is below 2 hours such as below 1 hour. Illustrative flow rates are within 0.01–100 nl/sec, typically 0.1–10 nl/sec. The same ranges of flow rate also apply to the flow in the restriction microconduit but the residence time may be different.

Guidelines for calculating the proper pressure drop means for a liquid of a particular viscosity may be obtained from the formula for Hagen-Poisseuille flow (fully developed laminar flow in a pipe/microconduit):

$$Q = \pi \cdot (p1-p2) \cdot Dh^4 / (128 \cdot \eta \cdot L)$$

where Q is the flow, p1–p2 is the pressure drop along the microconduit, Dh is the hydraulic diameter (=4×(cross-sectional area)/(wet perimeter), $\eta$ is the viscosity of the liquid and L is the length of the microconduit. Hydraulic diameter=hydrodynamic diameter of a microconduit in the priority application. Values obtained by application of this formula are only guidelines and typically requires testing before useful values for the pressure drop means can be accomplished.

Based on the formula the general guidelines given below are applicable.

For example, for a microcavity (104,204,304), the pressure drop means may be a porous material through which the liquid flow has to pass.

Yet further, for the restriction microconduit (105,205, 305), the pressure drop means typically contemplates that the largest cross-sectional area of this microconduit is less than the largest cross-sectional area of the inlet microconduits (102,103,202,203,302,303) or the microcavity (104, 204,304) with preference for $\leq 0.25$, such as $\leq 0.10$. Preferentially, these ranges apply for $\geq 10\%$, such as in $\geq 50\%$, of the length of a restriction microconduit, often with absolute preference for $\geq 90\%$ or the whole length of the restriction microconduit. The restriction microconduit typically ends when its cross-sectional area becomes larger than the smallest cross-sectional area of the shortest inlet microconduits (102,103,202,203,302,303) or the microcavity (104,204,304), for instance $\geq 4$ times or 10 times larger.

Other kinds of pressure drop means are also possible in the outlet microconduits (105,205,305). For example, the inner surface of the restriction microconduit, for instance, may be rougher than the inner surfaces upstream the restriction microconduit, such as upstream the microcavity, and/or the length of the restriction microconduit (105,205,305) may be greater, such as $\geq 5$ times or $\geq 10$ times, the length of the shortest inlet microconduit, possibly plus the length of the microcavity.

The term "length" of a microcavity or a microconduit refers to the distance inside the microchannel structure between the most downstream and the most upstream position of a microcavity/microconduit, or the difference in radial distance for these two positions. An inlet microconduit typically stretches from the restriction microconduit, or from the microcavity (if present) to and also encompasses the closest valve function, anti-wicking function or branch in the upstream direction, or if none of these functions are present to the closest inlet port.

The pressure drop in the restriction microconduit (105) is proportional to its length and inversely proportional to its hydraulic cross-sectional area. An increase in length of the restriction microconduit may thus compensate for an increase in its cross-sectional area and vice versa.

The invention is particularly adapted to liquids that have a viscosity that is within the range of 10–1000% of the viscosity of water, i.e., $10^{-4}$–$10^{-2}$ Ns/m$^2$. The liquids are typically aqueous.

2. Common Flow Control

The term "common flow control" means that when a driving force for a liquid flow is applied in one part of a microchannel structure, there will also be applied a driving force for liquid flow in the corresponding part of each of the other microchannel structures of the device. The driving force in the individual microchannel structures derives from the same source, e.g., spinning the device if centrifugal force is the driving force. Moreover, an increase or a decrease in driving force in one microchannel structure is paralleled with an increase or a decrease in the other microchannel structures. The size of the force (and the liquid flow rate) may differ between different microchannel structures for which common flow control is applied. In centrifugal based systems, for instance, the designs of the microchannel structures may differ and/or the microchannel structures may be placed at different radial distances.

Common flow control primarily refers to the flow through the microcavity (104,204,304). This in particular applies when a reaction is to take place locally in the microcavity, for instance when a solid phase that exhibits an immobilized reactant that is to interact with a reactant which is present in the liquid flow passing the solid phase/microcavity. See further elsewhere in this specification. Common flow control may be less critical in other parts of the structures and/or for other steps of a method performed in the innovative microfluidic device.

The liquid flow may be driven by distinct means that either is present in or external to the device. Thus, liquid flow may be created by electroosmosis, micropumps, expanding gas etc., Another alternative is to use forces such as capillary force and inertia force including gravitational force and centrifugal force to drive the liquid, i.e., forces that do not require any means on the microfluidic device. Capillary flow is typically not under common flow control since it depends on local surface characteristics.

According to a preferred variant of the invention, common flow control is accomplished by spinning a microfluidic device in which the microchannel structures are oriented from an inward position to an outward position in relation to an axis of symmetry (spin axis) of a substrate comprising the device. Typically the spin axis coincides with an axis of symmetry of the device as discussed below. Common flow control also includes that centrifugal force is used to create a sufficient local hydrostatic pressure within a structure to drive a liquid aliquot through an outward (downward) and/or an inward (upward) bent of a microchannel structure. See for instance WO 0146465. The use of centrifugal force for driving a liquid flow has been described in the publications in the name of Gyros, Gamera Biosciences and Abaxis that are referenced above, and also incorporated herein by reference.

Typical spinning speeds are within the interval 50–25000 rpm, such as 50–15000 rpm. The spinning speed within a given protocol may vary, for instance comprise sequences with individual ramps of acceleration, deceleration, and constant spinning. It may be beneficial to include a pulse of increased spinning at certain positions.

B. Microfluidic Device

A microfluidic device comprises at least one, two or more enclosed microchannel structure through which liquid flow is used for the transport of reactants The terms "microformat", "microchannel" etc., contemplate that a microchannel structure comprises one or more cavities and/or channels that have a depth and/or a width that is $\leq 10^3$ µm, preferably $\leq 10^2$ µm. The volumes of microcavities are typically $\leq 1000$ nl (=nl-range), such as $\leq 500$ nl or $\leq 100$ nl or $\leq 50$ nl, but may also be larger, i.e., in the interval 1–1000 µl, such as 1–100 µl or 1–10 µl.

Liquid aliquots used in the invention typically have volumes in the range $\leq 5000$ nl, such as $\leq 1000$ nl or $\leq 500$ nl or $\leq 100$ nl or $\leq 50$ nl, but may also be in other intervals, such as 1–1000 µl, or 1–100 µl or 1–10 µl. Dispensed aliquots are typically sucked completely into the microchannels by capillarity before some other driving force is applied to transport them downstream in the microchannel structures, typically stepwise with one step for each functional unit.

In specific embodiments, it is intended that cross-sectional areas are perpendicular to the intended flow direction.

Yet further, the present invention is primarily intended for geometric arrangements in which the microchannel structures are present in a substrate (e.g., a microfluidic device) that has an axis of symmetry that may be used as a spin axis. The substrate in this context may be the microfluidic device as such or a disc holder on which a microfluidic disc comprising the microchannel structures may be placed. The innovative structural unit is in the upstream direction communicating with a unit, which delivers liquid to the unit via the inlet microconduit (302,303) and communicates with or comprises an inlet port. In the downstream direction, the innovative structural unit communicates with an outlet port via the restriction microconduit (205,305). Each microchannel structure is oriented either fully or partly in an outward direction relative to the axis of symmetry (spin axis) thereby enabling centrifugal force to be used for driving liquid flow. Yet further, it is contemplated that the microchannel structures and microconduits may or may not be oriented in a plane perpendicular to the axis of symmetry (spin axis).

In centrifugal systems a "higher" or an "upper" level/position (inner position) will be at a shorter radial distance (inner position) compared to a "lower" level/position (outer position). Similarly, the terms "up", "upward", "inwards", and "down", "downwards", "outwards" etc., will mean towards and from, respectively, the spin axis. This applies if not otherwise is specified. With respect to other arrangement/substrates and conventional driving forces, i.e., gravity force, externally applied pressure, electro-osmotically driven flows etc., these terms have their conventional meaning.

Axes of symmetry are n-numbered (Cn) and may coincide with a spin axis. n is an integer between 2 and $\infty$, preferably 6, 7, 8 and larger, for instance $\infty$. In preferred cases microfluidic device as such may have a circular, cylindrical, spherical or conical symmetry (C$\infty$).

The preferred devices are typically disc-shaped with sizes and forms similar to the conventional CD-format, e.g., in the interval from 10% up to 300% of the conventional CD-radii.

Figure 2A:
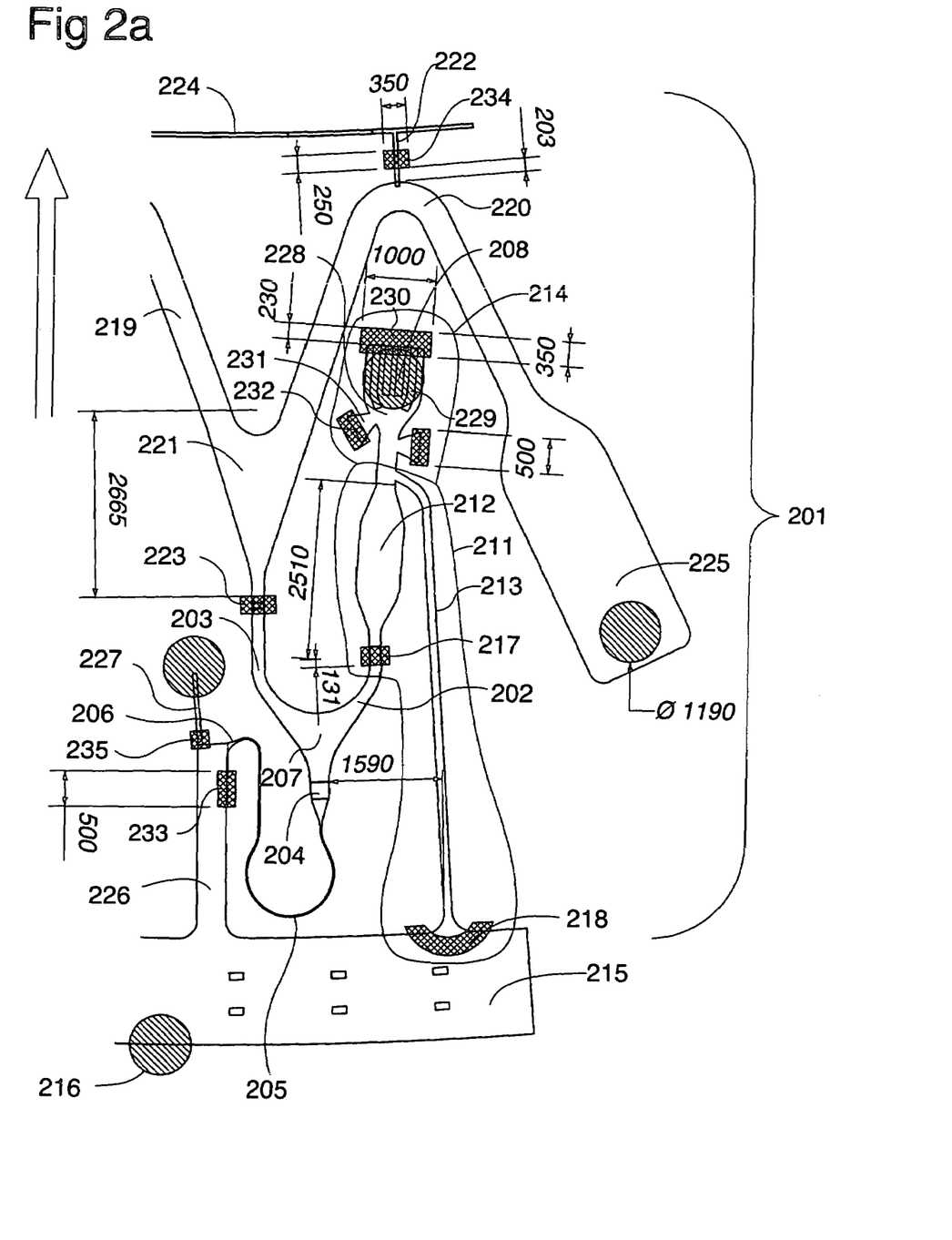
FIGS. 2A and 2B illustrate a variant of a preferred microchannel structure that has a narrow microconduit that create a significant pressure drop. This variant has been used for the model study presented in the experimental part.
Figure 2B:
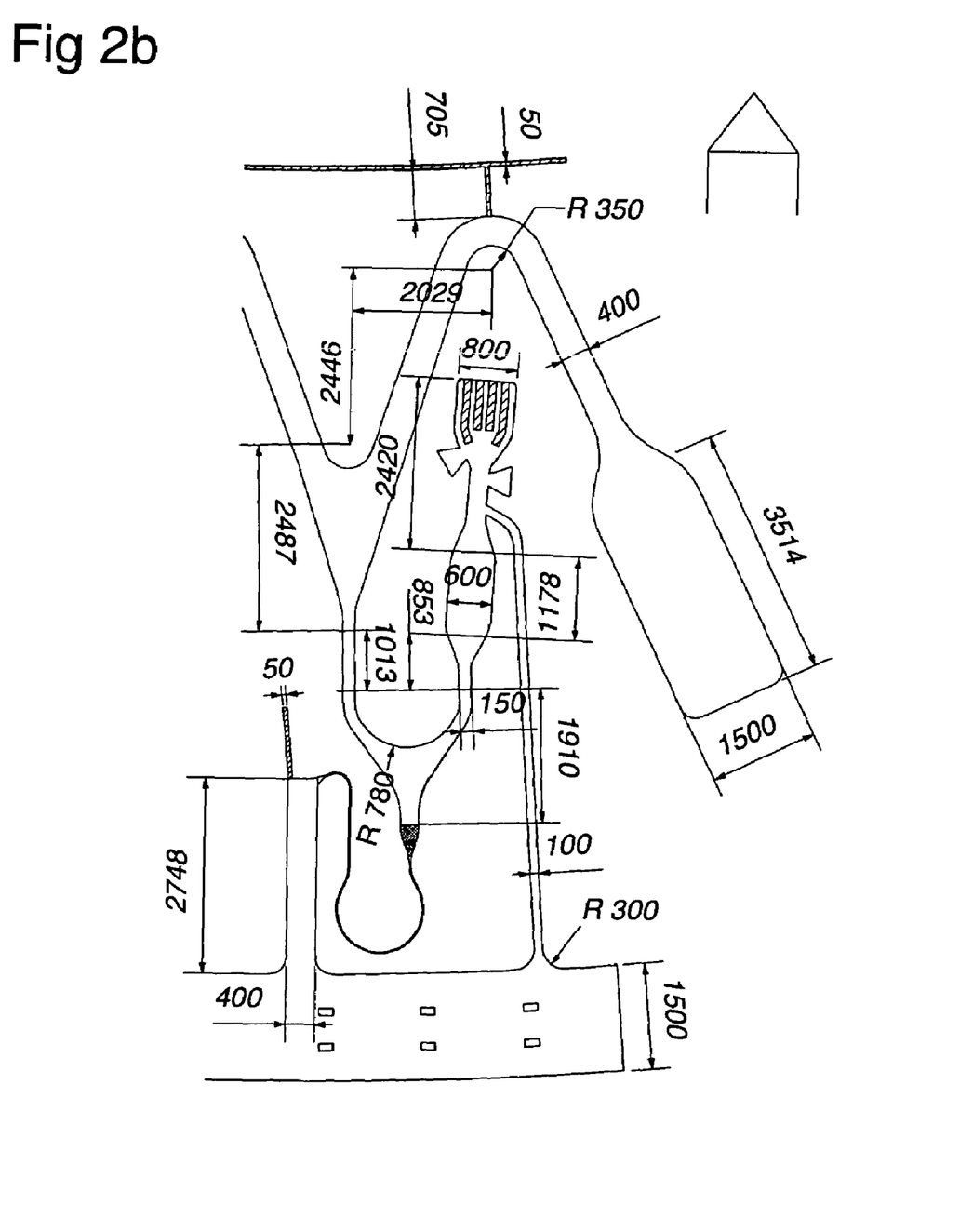
Figure 3:
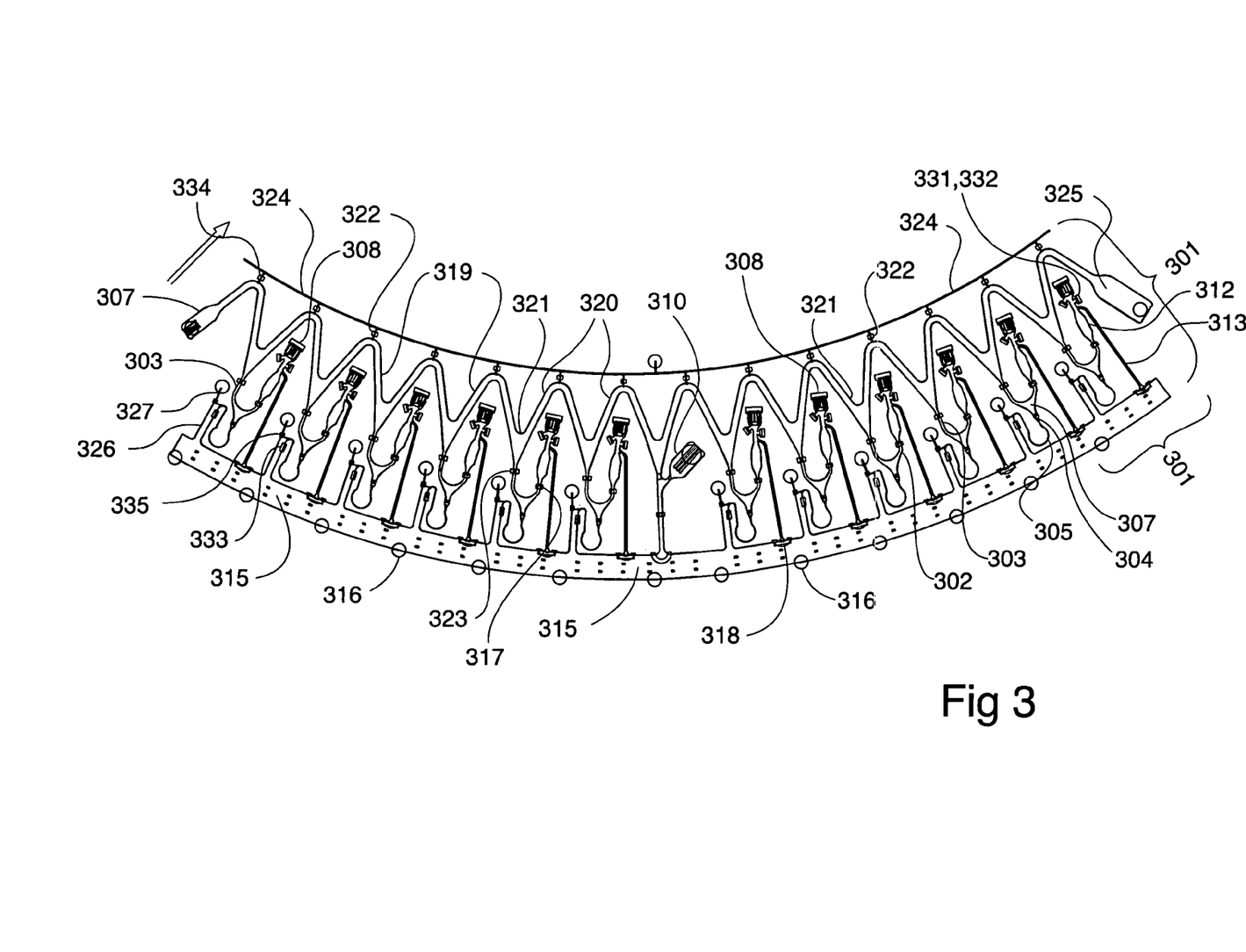
FIG. 3 illustrates a set of microchannel structures of the same kind as used in the experimental part. The structures are linked together by a common distribution channel and a common waste channel.

FIGS. 2A–B and 3 illustrate a microchannel structure (201,301) of the invention adapted for a heterogeneous reaction. The structure comprises a microcavity (204,304) (reaction microcavity) in which there may be an immobilized reactant (reactant 1) that is to react with a reactant (reactant 2) that is present in a liquid flow passing through the microcavity. As already discussed for the general innovative concept (FIG. 1), the microcavity (204,304) is connected to one or more inlet microconduits (202,203) each of which communicates with an inlet port (208,308,310), and a restriction microconduit (205,305) with an outlet end (206,306) which in turn communicates with an outlet port (216,316).

The inlet port (208,307,308) may be located at a shorter radial distance (higher level) and the outlet port (216,316) at a larger radial distance (lower level) than the microcavity (204,304). By utilizing capillary force and/or other non-centrifugal forces for the introduction of a liquid into a microchannel structure, inlet ports may be located at in principle any radial distance (level) (e.g., more remote from the axis of symmetry (spin axis) than an outlet port and/or than the microcavity (not shown). Outlet ports may be located at a shorter radial distance (higher level) than the microcavity (204,304) as illustrated by port (225,325).

If there are two or more inlet microconduits (202,203 and 302,303), they typically merge at the start of the restriction microconduit or before the microcavity (204,304), if it is present. In the case the microcavity (204,304) contains a solid phase in form of particles, the trespass into the restriction microconduit (205,305) typically is a sharp drop in the cross-sectional area that prevents the particles from passing into the restriction microconduit.

For centrifugal systems, two inlet microconduits (202,203 and 302,303) typically form a downward bent (207,307) with shanks corresponding to the inlet microconduits (202, 203 and 302,303). The restriction microconduit (205,305) is connected to the lower part of the bent, for instance as illustrated in FIGS. 2–3 via the microcavity (204,304).

An inlet microconduit (202,302) may be connected to an inlet port (208,308) via a volume-defining unit (211) that comprises a metering microcavity (212,312) connected to one of the inlet microconduits (202,302), an overflow channel (213,313) that starts in a narrow conduit part between the metering microcavity (212,312) and the inlet unit (214) and ends in a waste function, for instance comprising a common waste reservoir/channel (215,315). The waste function may have one or more outlet ports (216,316). The volume-defining unit (211) typically comprises valve functions (217, 218,317,318) that are associated with the overflow channel (213,313) and with the outlet end of the metering microcavity (212,312), respectively. For centrifugal systems, these valve functions are typically passive and are preferably based on local changes in surface characteristics. The valve function (218,318) is at a larger radial distance than the valve function (217,317). This means that the positions of these valves are selected to support that liquid in the overflow channel (213,313) is passed into the waste function at a lower spinning speed than liquid in the metering microcavity (212,312) is passed into the inlet microconduit (202,303). A volume-defining unit of this kind (211) is primarily intended for liquid aliquots that are to be introduced with high accuracy with respect to volume. This means liquid aliquots that contain an analyte and/or any other reagent that has to be delivered with a high accuracy. See PCT/SE02/531 (Gyros AB) and PCT/SE02/01539 (Gyros AB), which are incorporated by reference herein.

An alternative functional unit that may be connected to one of the inlet microconduits (203,303) is a unit for simultaneously distributing liquid aliquots to several separate microchannel structures. The unit may be in the form of a distribution channel (219,319) that is common for several microchannel structures (201,301). For centrifugal system the channel may have alternating upper and lower parts (220,320 and 221,321, respectively) with an inlet vent (222,322) (top vent) to ambient atmosphere in each upper part (220,320) and a liquid communication with a valve function (223,323) in each lower part (221,321) to one of the inlet conduits (203,303) of a microchannel structure (201, 301). The top vents (222,322) may communicate with ambient atmosphere via a common venting channel (224, 324). The distribution channel may have one or more inlet ports (307,310) and one or more outlet ports (225,325) (only one shown) connected to separate upper parts. Several units may be linked together in series via ending upper parts as illustrated in FIG. 3. Each of the top vents may be combined or replaced with anti-wicking means in the lower wall of the upper part connected to the top vent concerned. This kind of distribution system typically is used when identical liquids are to be distributed as separate aliquots to different microchannel structures. Typical liquids are buffers, reagents, washing liquids, samples etc., By utilizing distribution systems in which the lower parts (221,321) differ in volume, the volume of the aliquots will differ between the microchannel structures. See PCT/SE02/531 (Gyros AB) and PCT/SE02/01539 (Gyros AB), which are incorporated by reference herein.

The outlet end (206,306) of a restriction microconduit (205,305) may mouth into a microconduit (226,326) with enlarged cross-sectional area and communicating with ambient atmosphere as is illustrated with a waste function in FIGS. 2–3. This enlarged microconduit may also have other functions, for instance as microchamber/microcavity for controlled mixing and addition of reactants such as in microtitration, organic microsynthesis, etc.

In the case that a waste function is linked directly to the restriction microconduit, the waste function may comprise a waste microconduit (226,326) (belonging to the microchannel structure), which in turn may mouth into a common waste microconduit/reservoir (215,315). Alternatively, the outlet end (206,306) may open directly into a common waste microconduit/reservoir, or into ambient atmosphere (not shown). The cross-sectional area, typically the largest cross-sectional area, of the waste function in the proximity of the outlet opening (206,306) should be larger than the cross-sectional area of the restriction microconduit (205,305) at its outlet end (206,306), e.g., $\geq 4$ or $\geq 10$ times larger. These ranges also apply for enlarged microconduits (microcavities) that are located to this position but have other functions. The outlet end (206,306) of the restriction microconduit (205, 305) typically is at the same or at a higher level than the joint between an inlet microconduit and the restriction microcavity, or than the microcavity (204,304) (if present) (preferably its top part). The above discussions, which are incorporated herein, also apply to a centrifugal system that utilizes passive valves at the inlet ends of the innovative structural unit.

A waste function typically has anti-wicking means (233, 235,333,335) in close proximity to the outlet end (206,306) in one or more edges extending from the restriction microconduit (205,305) into the waste function, typically in edges that have a downward direction. In close proximity, contemplates that these anti-wicking means always are above the lowest part of the restriction microconduit including within the outlet end (206,306) (not shown). In the case that the restriction microconduit (205,305) is connected to a waste microconduit (226,326), there is preferably a vent (227,327,235,335) to ambient atmosphere in the waste microconduit (226,326). This vent typically is at approximately the same level as or at a higher level than the outlet end (106) of the restriction microconduit (105) and may contain anti-wicking means (235,335). Yet further, the positioning of anti-wicking means in the waste function also applies if the enlarged microconduit (226,326) does not comprise a waste function.

The principles outlined for pressure drop in the microchannel structures have lead to the design of the microchannel structures given FIGS. 2–3; such as, reaction microcavities (204,304) with a depth of 100 µm and width of 250 µm; and restriction microconduits (205,305) with a depth of 10 µm, a width of 20 µm and a length of 4.56 mm.

Yet further, other parts of the microchannel structures have a depth of 100 µm. For the proper balancing out of inter-channel variations in flow resistance, there are hydrophobic surface breaks (233,333 and/or 235,335) and a vent (227,327) to ambient atmosphere.

The inlet ports (208,308) are preferably connected to an inlet microcavity (228,328), which typically is narrowing inwards the microchannel structure and has longitudinal projections (ridges) (229) in the flow direction. These ridges will facilitate quick transport of a dispensed liquid aliquot into the interior of an inlet unit. The inlet ports also may have a non-wettable area (typically hydrophobized) (230, cross-hatched) that will direct a dispensed liquid into the inlet unit (214). The same applies also to the other inlet ports (307,310).

The microchannel structures may be equipped with anti-wicking means at selected positions in form of changes in surface characteristics that typically local and may be related to geometric surface characteristics (231) and/or chemical surface characteristics (232,233,235)(cross-hatched area). For aqueous liquids this means that the change is from hydrophilic to hydrophobic (hydrophobic surface breaks). The inlet vents (234,334,235,335) and the passive valves (217,223,317,323) comprise anti-wicking function. See WO 9958245, Amersham Pharmacia Biotech AB), WO 0185602 Åmic AB & Gyros AB and PCT/SE02/00531, PCT/SE02/01539 (plus the corresponding US application filed in parallel) which are incorporated herein by reference.

Valves are preferably passive (217,223,218,318,317,323), i.e., passage of a liquid will depend on the applied driving force and the physicochemical match between a liquid and the inner surface at the valve position. Thus, movable mechanical parts are needed, for example, capillary valves that are based purely on a change in geometric surface characteristics (WO 9615576 (David Sarnoff Res. Inst.) and WO 9807019 (Gamera) which are incorporated herein by reference. More particularly, preferred passive valves are based on a change in chemical surface characteristics, e.g., non-wettable surface breaks (hydrophobic surface breaks), possibly combined with changes in geometric surface characteristics. Other kinds of valves may also be used.

More details about inlet units, distribution units, volume-defining units, waste conduits, anti-wicking means and valves, in particular for centrifugal systems, are given in PCT/SE02/00531 and PCT/SE02/01539 (plus the US application filed in parallel), which are incorporated herein by reference.

Suitable microfluidic devices may be manufactured from a planar substrate surface comprising a plurality of uncovered microchannel structures that in a subsequent step are covered by another planar substrate (lid). See WO 9116966 (Pharmacia Biotech AB) and WO 0154810 (Gyros AB) which are incorporated herein by reference. At least one of the substrates may be transparent, e.g., the second substrate (lid). Both substrates are preferably fabricated from plastic material, e.g., plastic polymeric material.

Different applications require different surface characteristics. e.g., inner surfaces of the microchannel structures may require hydrophilization for transport of aqueous liquids and the like. See for instance WO 0056808 (Gyros AB) and WO 0147637 (Gyros AB), which are incorporated herein by reference. Typically an essential part of the inner surfaces should have water contact angles $\leq 90°$, such as $\leq 40°$ or $\leq 30°$ or $\leq 20°$ at the temperature of use, e.g., at least the surfaces of two or three of the inner walls enclosing a channel should comply with this range. Surfaces in passive valves, anti-wicking means, etc., are excluded from these general rules.

C. Microcavity

The microcavity (104,204,304) is preferably a straight microchannel that may be continuously widening and/or narrowing. At least a part of the wall of the microcavity may be transparent to allow for measuring of events taking place within the microcavity. Transparency is with respect to the principle used for measuring.

The microcavity (104,204,304) may comprise a solid phase, which may have either one or both of the functions: (a) carrying an immobilized reactant for a reaction to take place within the microcavity and/or (b) providing pressure drop means in the microcavity. Different reactants are discussed below. Additional functions for the solid phase are as a separation medium in size exclusion separation (gel chromatography, gel electrophoresis etc.), support medium to reduce convection and/or diffusion (electrophoresis such as isoelectrophoresis), support medium in affinity-based separations (often included in the function of item (a)), etc.

In the preferred variant the solid phase is a population of porous or non-porous particles that are packed to a bed, or a porous monolith that wholly or partly will occupy the interior of the reaction microcavity. In the case the solid phase comprises particles there should be a retaining means associated with the downstream end of the reaction microcavity. This means is preferably in the form of a constriction, e.g., in the form of a barrier, that prevents the particles from leaving the microcavity. The particle diameter/size should at least be of the same size as or larger than the smallest dimension of the opening in the constricted part. Another kind of retaining means is magnetic particles combined with an externally applied magnetic field.

A porous monolith may be fabricated in one piece of material or may comprise particles that are attached to each other. Yet further, a porous monolith may have pores that are large enough to permit mass transport of a reactant that is present in a liquid flow passing through monolith.

As used herein, the term "porous particles" refers to particles that can be penetrated by a particular reactant that is present in a liquid flow passing through a packed bed of the particles. This typically means Kav values within the interval of 0.4–0.95 for the reactant concerned. Non-porous particles have a Kav-value below 0.4 with respect to the same reactant. The particles may be spherical or non-spherical. With respect to non-spherical particles, diameters and sizes refer to the "hydrodynamic" diameters. Yet further, the particles are preferably monodisperse (monosized) by which is meant that the population of particles placed in a reaction microcavity has a size distribution with more than 95% of the particles within the range of the mean particle size ±5%. Populations of particles that are outside this range are polydisperse (polysized).

The solid phase may or may not be transparent. The material in the solid phase, e.g., the particles, is typically polymeric, for instance a synthetic polymer or a biopolymer. The term biopolymer includes semi-synthetic polymers comprising a polymer chain derived from a native biopolymer. The solid phase is typically hydrophilic in the case the liquid flow is aqueous. In this context hydrophilic encompasses that a porous solid phase, e.g., a packed bead, will be penetrated by water. The term also indicates that the surfaces of the particles shall expose a plurality of polar functional groups in which there is a heteroatom selected amongst oxygen, sulphur, and nitrogen. Appropriate functional groups can be selected amongst hydroxy groups, straight eythylene oxide groups ($[-CH_2CH_2O-]_n$, an integer >0), amino groups, carboxy groups, sulphone groups etc., with preference for those groups that are essentially neutral independent of pH, for instance within the interval of 2–12. A hydrophobic particle may be hydrophilized, for instance by introducing hydrophilic groups. See for instance the experimental part. The coating technique is similar to the technique presented in WO 9800709 (Pharmacia Biotech AB, Arvidsson & Ekström) which is incorporated herein by reference. The solid phase may also be the inner surfaces of the microcavity, but then its main function will be to provide support for an immobilized reactant.

The reactant that may be immobilized to the solid phase depends on the application to be performed in the microchannel structure. It may for instance be a reactant participating in an organic, an inorganic, a biochemical reaction etc. The reactant may thus be a catalytic system or a part of a catalytic system, such as a catalyst as such, a cocatalyst, a cofactor, a substrate or cosubstrate to the catalyst, an inhibitor, a promotor etc., with specific emphasis to the corresponding parts of enzymatic systems (enzyme, cocatalyst, cofactor, coenzyme, substrate, cosubstrate etc.). The term "catalytic system" also includes linked catalytic systems, for instance a series of systems in which the product of the first system is the substrate of the second catalytic system etc., and whole biological cells or part of such cells.

The reactant may be a so-called affinity reactant i.e., an affinity reactant that together with its affinity counterpart (affinity pair) is capable of forming an affinity complex held together by affinity bonds. Affinity bonds typically are based on: (a) electrostatic interaction, (b) hydrophobic interaction, (c) electron-donor acceptor interaction, and/or (d) bioaffinity binding. Bioaffinity binding typically is complex in nature and comprises e.g., a combination of interactions selected amongst variations of items (a)–(c).

Thus, in the present invention, an affinity reactant may thus: (a) be electrically charged or chargeable, i.e., contains positively charged nitrogen (e.g., primary, secondary, tertiary or quaternary ammonium groups, and amidinium groups) and/or negatively charged groups (e.g., carboxylate groups, phosphate groups, phosphonate groups, sulphate groups and sulphonate groups); (b) comprise hydrocarbyl groups and other hydrophobic groups; (c) comprise heteroatoms, possibly linked to hydrogen, and/or $sp^2$- and/or $sp^3$-hybridised carbon, or (d) comprise in combination variations of items (a)–(c).

A bioaffinity reactant is a member of a bioaffinity pair. Typical bioaffinity pairs are antigen/hapten and an antibody or an antigen binding fragment of the antibody mimetic of an antibody; complementary nucleic acids; immunoglobulin-binding protein and immunoglobulin (for instance IgG or an Fc-part thereof and protein A or G), lectin and the corresponding carbohydrate, biotin and (strep)avidin, etc. The term "bioaffinity pair" includes affinity pairs in which one or both of the members are synthetic, for instance mimicking a native member of a bioaffinity pair.

The term "affinity reactant" includes a reactant that is capable of reversible covalent binding, for instance by disulfide formation. Typical such reactants exhibit a HS— or a —S—SO$_n$— group (n=0,1 or 2, free valences bind to carbon). See U.S. Pat. No. 5,887,997 (Batista), U.S. Pat. No. 4,175,073 (Axén et al.), U.S. Pat. No. 4,563,304 (Axén et al.) and U.S. Pat. No. 4,647,655 (Axén et al.) which are incorporated herein by reference. The term "affinity reactant" also includes a reactant that is capable of binding via chelate formation, i.e., a reactant that exhibits a chelating group, possibly in chelate form with remaining chelating ability. Affinity reactants typically exhibit amino acid structure including peptide structure such as poly and oligopeptide structure, carbohydrate structure, nucleotide structure including nucleic acid structure, and lipid structure such as steroid structure, triglyceride structure, etc.

The techniques for immobilization of a reactant may be selected amongst techniques that are commonly known in the field. The linkage to the solid phase may be via covalent bonds, affinity bonds (for instance biospecific affinity bonds), physical adsorption (mainly hydrophobic interaction), etc. Examples of biospecific affinity bonds that can be used are bonds between strepavidin and a biotinylated affinity reactant (or vice versa), between an antibody and a haptenylated affinity reactant (or vice versa), etc.

D. Other Functional Units

A microchannel structure may also comprise additional units with separate or combined functions enabling e.g. (1) separation of particulate matter from a liquid aliquot introduced via an inlet port, (2) mixing of two liquid aliquots, and (3) detection of (a) a reactant that has passed through the microcavity (104,204,304), or (b) a component formed in the microcavity (104,204,304). Except for unit 3, these functional units, if present, may be present upstream the microcavity (104,204,304).

A unit for separation of particulate matter is typically positioned upstream a volume metering unit or the two units are combined in a common unit. Preferred separation units, volume metering units and mixing units are given in PCT/SE02/00531 and PCT/SE02/01539 (including the US application filed in parallel) which are incorporated herein by reference. A separation unit is typically combined with or present upstream a volume-metering unit. A mixing unit, if present, is typically present downstream a volume metering step.

E. Microchannel Structures having Restriction Microconduits Providing Different Pressure Drops The microfluidic device may contain microchannel structures that are essentially equal. The term equal in this context means that the structures are essentially identical except for differences in design of the restriction microconduits (105, 205,305) in order to allow them to provide different pressure drops.

In one variant of the innovative microfluidic devices, the microchannel structures are grouped into sets, each of which contains restriction microconduits which are designed for essentially the same pressure drop, e.g., have the same length and cross-sectional area. In other words, the intended pressure drop vary between the sets but is essentially the same within a set. A particular interesting variant is a microfluidic device which a) utilizes spinning and centrifugal force as discussed above to drive liquid flow; b) has the restriction microconduits within a set at the same radial distance relative to the spin axis of the device but at other radial distances if they belong to other sets; c) has the restriction microconduits designed for a lower pressure drop at a shorter radial distance than the restriction microconduits designed for a higher pressure drop; and d) has the radial distance for the restriction microconduits of different sets adjusted to provide the same flow rate through the restriction microconduit (102,103,202, 203,302,302,303) and microcavity (104,204,304) (if present) of all the microchannel structures of the microfluidic device.

An innovative centrifugal microfluidic device may thus comprise microchannel structures that are grouped into sets that differ with respect to the length and/or cross-sectional area of their restriction microconduits. Each of these sets may be arranged in an annular zone or sector thereof, that is concentric with the spin axis, for instance with restriction microconduits that are shorter and/or have a larger cross-sectional area at a shorter radial distance than restriction microconduits that are longer and/or have a smaller cross-sectional area. One advantage of this is that the same controlled flow rate and residence time easily can be accomplished in parallel within all the restriction microconduits/microcavities (105,205,305)/(104,204,304) of microchannel structures that are essentially equal in the device by properly adapting the radial distance between the annular zones and/or between the sectors of such zones. This is based on the fact that the centrifugal force (driving force) increases with an increase in radial distance.

In a second variant of a centrifugal microfluidic device, there are restriction microconduits, which are designed for different pressure drops and located at the same radial distance, i.e., in an annular zone concentric with the spin axis, or a sector of such a zone. In other words the same annular zone or sector may comprise restriction microconduits of different length and/or cross-sectional areas.

In a third variant, there are restriction microconduits, which are designed for the same pressure drop but located at different radial distances, i.e., in different annular zones that are concentric with the spin axis, or in sectors of such zones. In the second variant, the flow rate will differ between restriction microconduits/microcavities in the same annular zone. In the third variant, the flow rate will differ between restriction microconduits/microcavities of different annular zones.

These two variants and also other variants that are based on properly combining restriction microconduits designed for different pressure drops with selected combinations of radial distances for the restriction microconduits will enable performing experiments on a microfluidic device in parallel under different controlled flow conditions (flow rates and/or residence times).

E. Use of the Microfluidic Device

One of the uses of the innovative device is a method for creating a controlled liquid flow in parallel through a plurality of microchannel structures of a microfluidic device. The method comprises the steps of i) providing a microfluidic device which comprises two or more microchannel structures (201,301) each of which is defined herein; ii) providing a liquid aliquot in one of the one or more of the inlet microconduits (202,203,302,303) in each of the microchannel structures (201,301); iii) applying a driving force that creates a liquid flow that transport said aliquot through the outlet microconduit (205,305), possibly via the microcavity (204,304) (if present), of each of the microchannel structures (201,301).

Step (ii) includes among others that a larger aliquot is dispensed to a common inlet port and portioned into individual microchannel structures via a distribution unit, and/or that an aliquot is dispensed directly to each microchannel structure as illustrated in FIGS. 2 and 3.

The method is characterized in that a) the outlet microconduits (105,205,305) are restriction microconduits as defined above, b) the liquid flow created in step iii) is under common flow control; and c) the driving force is adjusted to give the flow rate that is required by the restriction microconduits (105,205,305), i.e., a flow rate within the interval given above that will give the pressure drop that the microconduits (105,205,305) are designed.

The various features of the microfluidic device discussed elsewhere in this specification further characterize sub-aspects of the method. This includes the characteristics of the liquid as such and of the liquid flow, e.g., viscosity, flow rate, residence time, inter-channel variation. The device utilizes in preferred variants spinning and centrifugal force for common flow control and for creating the liquid flow in step (iii).

Other uses of the device relate to applications carried out within the microchannel structures. Synthetic, analytical, preparative etc., applications within chemical and biological sciences such as organic and organic chemistry, biology, medicine, diagnosis, molecular biology etc. are typical examples.

In many cases the applications includes that one or more reactions are carried out within each of the microchannel structures, for instance with at least one reaction within the microcavity (104,204,304) or within a reaction microcavity in a downstream position (not shown), for instance linked directly to the outlet end of the restriction microconduit (205,305) but upstream the waste function, if present. The reactions, e.g., within the microcavity (104,204,304), may be: (a) homogeneous, i.e., between reactants (e.g., solutes) that are passing through the microcavity in a liquid flow, or (b) heterogeneous, i.e., between a reactant that is immobilized within the microcavity and a reactant (e.g., a solute) that is passing through the microcavity in a liquid flow. Typically the liquid flow is controlled and under common flow control as described elsewhere in this specification.

In specific aspects, an application may comprise a separation that may or may not comprise a reaction, for instance adsorptions that are based of an affinity reaction as defined herein, and size exclusion separations and electrophoresis that do not need to involve any reaction as such.

In general the innovative microfluidic device is well adapted to applications in which controlled mixing or controlled addition of reagents are needed, for instance microtitration and inorganic and organic chemical synthesis in the microformat. Microtitration and controlled addition of reagents may for instance take place in a separate reaction microcavity linked directly to the outlet end of the restriction microconduit (and upstream a waste function).

An important class of reactions that can be performed in the innovative microfluidic device comprises formation or dissociation of an affinity complex. Formation comprises that an affinity reactant that is immobilized to a solid phase (capturing reactant) is introduced into the microcavity prior to the reaction. During the reaction a liquid flow comprising an affinity counterpart to the immobilized reactant is passed through the microcavity. Dissociation comprises that an immobilized form of an affinity complex is introduced into the microcavity prior to the desired reaction is taking place. During the reaction a liquid flow providing conditions for dissociation is passed through the microcavity.

Typically the result of the reaction is followed as the formation of a product, as the formation or disappearance of an intermediate or as the consumption of a reactant etc. Various detector systems/reactions may be used, and measurement may be carried in reaction microcavity, e.g., microcavity (104,204,304), and/or in one or more detection microcavities downstream the microcavity in which the desired reaction is taking place. Measurements are typically made through a transparent "window". Alternatively, a product (including intermediate) and/or a remaining part of a reactant is transferred via an outlet port to an external instrument for measurement.

Important reaction and detection systems as well as important applications are described in PCT/SE02/0537 (Gyros AB), which is incorporated herein, that also contains experiments verifying the usefulness of the innovative microfluidic device.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Yet further, all patent applications and issued patents that are referenced herein are incorporated herein by reference.

What is claimed is:

1. A microfluidic device which comprises a first set having two or more microchannel structures, each of which comprises a structural unit comprising one or more inlet microconduits, a microcavity, an outlet microconduit downstream said one or more microcavity, and a flow path for a liquid passing through either of said inlet microconduits, said microcavity and said outlet microconduit, wherein each outlet microconduit in said two or more microchannel structures is a restriction microconduit having a pressure drop means, wherein the pressure drop means comprises a cross-sectional area of the restriction microconduit that is $\leqq 0.25$ of the largest cross-sectional area of the inlet microconduits or of the microcavity in each of said microchannel structures and/or the length of the restriction microconduit is $\geqq 4$ times the length of the inlet microconduit or the microcavity in each of said microchannel structures.

2. The microfluidic device of claim 1, further comprising a pressure drop means in the microcavity.

3. The microfluidic device of claim 1, wherein the pressure drop along each of the restriction microconduits levels out inter-channel variations in flow resistance in upstream positions.

4. The microfluidic device of claim 1, wherein the pressure drop along each of the restriction microconduits levels out inter-channel variations in flow resistance in upstream and downstream positions of the structural unit comprising the restriction microconduit.

5. The microfluidic device of claim 2, wherein the pressure drop means in the restriction microconduit and the microcavity, in each of the microchannel structures is capable of giving an inter-channel variation in residence time in the microcavities which is within the mean residence time ±90% for a flow rate within the range 0.01–100 nl/sec of a liquid having a viscosity within the range of $10^{-4}$–$10^{-2}$ Ns/m$^2$.

6. The microfluidic device of claim 2, wherein said pressure drop means in the microcavity comprises a porous bed, wherein the porous bed comprises beads that are porous or non porous.

7. The microfluidic device of claim 6, wherein the porous bed comprises beads that are monosized or polysized.

8. The microfluidic device of claim 2, wherein said pressure drop means in the microcavity comprises a porous bed that is monolithic.

9. The microfluidic device claim 1, wherein the outlet end of the restriction microconduit is in registry with an enlarged microconduit, which in the downstream direction communicates with ambient atmosphere via at least one outlet port and has a cross-sectional area that is $\geqq 4$ times larger than the cross-sectional area of the restriction microconduit at its joint to the restriction microconduit.

10. The microfluidic device claim 1, wherein the device is designed for utilizing centrifugal force created by spinning the device around a spin axis for creating liquid flow.

11. The microfluidic device of claim 9, wherein the joint between said restriction microconduit and said enlarged microconduit is at least at the same level as the connection between said one or more inlet microconduits and the restriction microconduit, or the top part of the microcavity, and said enlarged microconduit has an inlet vent for ambient atmosphere at its upper part.

12. The microfluidic device claim 11, wherein the enlarged microconduit has anti-wicking means at least in edges coming from the restriction microconduit and in close proximity to the outlet end of the restriction microconduit, and the anti-wicking means is in the form of hydrophobic surface breaks.

13. The microfluidic device of claims 1, wherein at least one of said inlet microconduits is connected to a volume-defining unit.

14. The microfluidic device of claims 1, wherein said microcavity has a volume within the range of 1–1000 nl.

15. The microfluidic device of claim 1, wherein the device is adapted for using centrifugal force for driving a liquid flow by spinning the device around a spin axis, and the restriction microconduits of said two or more microchannel structures are located at the same radial distance relative to the spin axis.

16. The microfluidic device of claim 1, wherein the device is adapted for using centrifugal force for driving a liquid flow by spinning the device around a spin axis, and the device comprises a second set having two or more microchannel structures, each of which has the structural unit with a restriction microconduit of a length and/or a cross-sectional area that are/is different from the length and/or cross-sectional area of the restriction microconduits of the first set of microchannel structures.

17. The microfluidic device of claim 16, wherein at least two of the restriction microconduits of the microchannel structures of the second set are located at the same radial distance as the restriction microconduits of the first set.

18. The microfluidic device of claims 16, wherein the device comprises a third set having two or more microchannel structures, each of which has the structural unit with a restriction microconduit of the same length and/or cross-sectional area as the restriction microconduit of the first set and that at least one of the restriction microconduits of the third set are located at a radial distance that is different from the radial distance of the restriction microconduits of the first set.

19. The microfluidic device of claims 16, wherein the restriction microconduits and the microcavity are designed for a liquid flow rate in the range of 0.01–100 nl/sec and/or a residence time in the microcavity of $\geqq 0.010$ sec.

20. A method for creating a controlled liquid flow in parallel through a plurality of microchannel structures of a microfluidic device, said method comprises the steps of:
(a) providing a microfluidic device which comprises said plurality of microchannel structures, each of which comprises a structural unit which comprises one or more inlet microconduits, a microcavity, and an outlet microconduit downstream said microcavity, and a flow path for a liquid passing through either of said inlet microconduits, said microcavity and said outlet microconduit;
(b) providing a liquid aliquot in at least one of said one or more inlet microconduits in each of the microchannel structures; and
(c) applying a driving force that creates a liquid flow that transports each of said aliquot through the microcavity and the outlet microconduit in each of the microchannel structures;
wherein the outlet microconduits are restriction microconduits each of which has a pressure drop means capable of creating a pressure drop that levels out inter-channel variations in flow resistance in positions upstream of said restriction microconduit, the liquid flow created in step (c) is under common flow control, and the flow rate created in step (c) for each of the structural units is adjusted to give the pressure drop in the restriction microconduits.

21. The method of claim 20, wherein the pressure drop means comprises a cross-sectional area of the restriction microconduit that is $\leq 0.25$ of the largest cross-sectional area of the inlet microconduits or of the microcavity in each of said microchannel structures and/or the length of the restriction microconduit is $\geq 4$ times the length of the inlet microconduit or the microcavity in each of said microchannel structures.

22. The method of claim 20, wherein the flow rate is adapted so that the inter-channel variation in residence time in the microcavities is within the mean residence time ±90% for a flow rate within the range 0.01–100 nl/sec of a liquid having a viscosity within the range of $10^{-4}$–$10^{-2}$ Ns/m$^2$.

23. The method of claim 20, wherein the device is adapted for using centrifugal force for driving a liquid flow by spinning the device around a spin axis, and the restriction microconduits of said two or more microchannel structures are located at the same radial distance relative to the spin axis.

24. The method of claim 20, wherein the liquid flow rate is in the range of 0.01–100 nl/sec and/or a residence time in the microcavity of $\geq 0.010$ sec.

25. The method of claim 20, wherein said microcavity has a volume of 1 nl to 100 µl.

26. The method of claim 20, wherein said aliquot has a volume of 1 nl to 100 µl.

27. The method of claim 20, wherein said microcavity comprises a porous bed.

28. The microfluidic device of claim 1, wherein the pressure drop means comprises a cross-sectional area of the restriction microconduit that is $\leq 0.25$ of the largest cross-sectional area of the inlet microconduits in each of said microchannel structures and/or the length of the restriction microconduit is $\geq 4$ times the length of the inlet microconduit in each of said microchannel structures.

29. The microfluidic device of claim 1, wherein the pressure drop means comprises a cross-sectional area of the restriction microconduit that is $\leq 0.25$ of the largest cross-sectional area of the microcavity in each of said microchannel structures and/or the length of the restriction microconduit is $\geq 4$ times the length of the microcavity in each of said microchannel structures.

30. The method of claim 20, wherein the pressure drop means comprises a cross-sectional area of the restriction microconduit that is $\leq 0.25$ of the largest cross-sectional area of the inlet microconduits in each of said microchannel structures and/or the length of the restriction microconduit is $\geq 4$ times the length of the inlet microconduit in each of said microchannel structures.

31. The method of claim 20, wherein the pressure drop means comprises a cross-sectional area of the restriction microconduit that is $\leq 0.25$ of the largest cross-sectional area of the microcavity in each of said microchannel structures and/or the length of the restriction microconduit is $\geq 4$ times the length of the microcavity in each of said microchannel structures.

* * * * *